US005874415A

United States Patent [19]
Kufe et al.

[11] Patent Number: 5,874,415
[45] Date of Patent: Feb. 23, 1999

[54] ENHANCER SEQUENCE FOR MODULATING EXPRESSION IN EPITHELIAL CELLS

[75] Inventors: Donald Kufe, Wellesley; Miyako Abe, Boston, both of Mass.

[73] Assignee: Dana-Farber Cancer Institute, Inc., Boston, Mass.

[21] Appl. No.: 465,981

[22] Filed: Jun. 6, 1995

Related U.S. Application Data

[62] Division of Ser. No. 324,465, Oct. 17, 1994, Pat. No. 5,565,334, which is a continuation of Ser. No. 999,742, Dec. 31, 1992, abandoned.

[51] Int. Cl.$^6$ .......................... A01N 43/04; A61K 38/16; C07H 21/04
[52] U.S. Cl. .............................. 514/44; 514/2; 536/24.1; 536/24.5
[58] Field of Search ................................. 435/69.1, 70.1, 435/70.3, 69.2, 183, 240.2, 243, 252.3, 320.1, 325; 536/23.1, 23.2, 23.5, 23.7, 23.72, 23.74, 24.1, 24.5; 514/44, 122

[56] References Cited

U.S. PATENT DOCUMENTS

| | | | |
|---|---|---|---|
| 4,497,796 | 2/1985 | Salser et al. | 424/95 |
| 4,740,461 | 4/1988 | Kaufman | 435/69.1 |
| 5,080,898 | 1/1992 | Murphy | 424/94.1 |
| 5,565,334 | 10/1996 | Kufe et al. | 435/69.1 |

FOREIGN PATENT DOCUMENTS

WO 91/09867  7/1991  WIPO .

OTHER PUBLICATIONS

Abe et al., Characterization of cis–acting elements regulating transcription of the human DF3 breast carcinoma–associated antigen (MUC1) gene, Proc. Natl. Acad. Sci. USA 90:282–286, 1993.

Manome et al., Enhancer Sequences of the DF3 Gene Regulate Expression of the Herpes Simplex Virus Thymidine Kinase Gene . . . of Human Breast Cancer Cells to Ganciclovir, Cancer Research 54:5408–5413, 1994.

Abe et al., Sequence Analysis of the 5' Region of the Human DF3 Breast Carcinoma–associated Antigen Gene, Bio. Biophys. Research Comm. 165:664–649, 1989.

Lundy et al., Monoclonal Antibody DF3 Correlates with Tumor Differentiation and Hormone Receptor Status in Breast Cancer Patients, Breast Cancer Res. Treat. 5:269–276, 1985.

Abe et al., Structural Analysis of the DF3 Human Breast Carcinoma–associated Protein, Cancer Res. 49:2834–2839, 1989.

Abe et al., Identification of a Family of High Molecular Weight Tumor–associated Glycoproteins, J. Immun. 139:257–261, 1987.

Abe et al., Transcriptional Regulation of DF3 Gene Expression in Human MCF–7 Breast Carcinoma Dells, J. Cell. Physio. 143:226–231, 1990.

Abe et al., Sodium Butyrate Induction of Milk–related antigens in Human MCF–7 Breast Carcinoma Cells, Cancer Res. 44:4574–4577, 1984.

Hug et al., Liposomes for the Transformation of Eukaryotic Cells, Biochim. Biophys. Acta 1097:1–17, 1991.

Neyfakh et al., Efflux–mediated Multidrug Resistance in Bacillus Subtilis: Similarities and Dissimilarities with the Mammalian System, Proc. Natl. Acad. Sci. USA 88:4781–4785, 1991.

McGrath et al., The Yeast STE6 Gene Encodes a Homologue of the Mammalian Multidrug Resistance P–Glycoprotein Nature 340:400, 1989.

Melani et al., Inhibition of Proliferation by c–myb Antisense Oligodeoxynucleotides in Colon Adenocarcinoma Cell Lines that Express c–myb, Cancer Research 51:2897–2901, 1991.

Gutierrez et al., Gene Therapy for Cancer, The Lancet 339:715–721, 1992.

Struhl, Deletion Mapping a Eukaryotic Promoter, Proc. Natl. Acad. Sci. USA 78:4461–4465, 1981.

von Zonneveld et al., Type 1 Plasminogen Activator Inhibitor Gene: Functional Analysis and Glucocorticoid Regulation of its Promoter, Proc. Natl. Acad. Sci. USA 85:5525–5529, 1988.

Sherman et al., Ionizing Radiation Regulates Expression of the c–jun Protooncogene, Proc. Natl. Acad. Sci. USA 87:5663–5666, 1990.

George et al., (1988) in Macromolecular Sequencing and Synthesis (Alan R. Liss, Inc., New York) pp. 127–149.

Lancaster et al., Structure and Expression of the Human Polymorhpic Epithelial Mucin Gene: an Expressed VNTR Unit, Biochm. Biophys. Res. Comm. 173:1019–1029, 1990.

Vlcek et al., Pseudorabies Virus Immediate–Early Gene Overlaps with an Oppositely Oriented Open Reading Frame: Characterization of Their Promoter and Enhancer Regions, Virology 179:365–377, 1990.

Orkin Report & Recommendations of The Panel To Assess The NIH Investment In Research on Gene Therapy, 1995.

*Primary Examiner*—Nancy Degen
*Attorney, Agent, or Firm*—Fish & Richardson P.C.

[57] ABSTRACT

Isolated DNA encompassing the DF3 enhancer as well as a sequence encoding a heterologous polypeptide provides epithelial tissue-selective gene expression of the heterologous polypeptide, useful in methods of therapy.

20 Claims, 8 Drawing Sheets

FIG. 1A

```
5'-
-1656  GCTTCCGTGC GCCTAGAGCG CAGCCTGCGA CTGCGGGACC CAACAACCAC GTGCTGCCGC GGCCTGGGAT AGCTTCCTCC CCTCTGGCAC TGCTGCCGCA
-1556  CACACCTCTT GGCTGTCGCG CATTACGGAC CTCACGTGTG CGCCTACGTC CTTTTGCCCC CCCAATACCA CCCCATATCCA CTCTGCTCCC CAAAGATAG
-1456  TTCTGTGTCC GTAAATCCCA TTCTGTCACC CCACCTACTC TCTGCCCCCC CCTTTTTTGT GGCCTAGCTG AGTCTTGTCC TGTCGCCCAG GCTGGAGTGC
-1356  AATGGCGCGA TCTCGGCTCA CTGCAAACTC CGCCTCCCGG GTTCAAGCGA TTCTCCTGCC TCAGCCTCCT GAGTAGCTGG GGTTACAGCG CCCGCCACCA
-1256  CGCTCGGCTA ATTTTTGTAG TTTTTAGTAG AGACGAGGTT TCACCATCTT GGCCAGGCTG GTCTTGAACC CCTGACCTTG TGATCCACTC GCCTGGCCT
                                                      NF-1                         ER               SP1
-1156  TCCAAAGTGT TGGGATTACG GCCGTGACGA CCGTGCCACG CTCTTAAGTA CCCGATCTGC CTCTTAAGTA CATAACGGCC GTGTCCAACT CCCCGCCCA
                AP-1
-1056  CGTTCCAACG TCCTCTCTCA CATACCCTCC TGCCCCTTCC ACATACCTCA GGACCCCACC CGCTTAGCTC CATTTCCTCC AGACGCCACC ACCACGCGTC
-956   CCGGAGTGCC CCCTCCTAAA GCTCCCAGCC GTCCACCATG CTGTGCGTTC CTCCCCTCCT GGCCACGGCA GTGACCTTC TCTCCCGGGC CCTGCTTCCC
                                                              AP-1  SP1              ER
-856   TCTCGCGGGC TCTCGCTGCC TCACTTAAGC AGCGCTGGCC TTACTCCTCT CGCCCCGTC CGAGCGGGCC CTCAGCTTGC GCGGCCCAGC CCCGCAAGGC
            ER             SP1
-756   TCCCCGTGAC CACTAGAGG CGGGAGGAGA TGGCAAGGAA GGACCCTAGG GTTCATGGA GCCCAGGTTT ACTCCCTTAA
                 AP-3                                              SP1
-656   GTGGAAATTT CTTCCCCCAC TCCCTCCTTG GCTTTCTCCA AGAGGGAAC CCAGGCTGCT GGAAAGTCG GCTGGGCGG GGACTGTGGG TTTCAGGGTA
                                                             AP-3       AP-2
-556   GAACTGCGTG TGAACGGGA CAGGGAGGGA TTAGAAGGT GGGGCTATTC CGGGAAGTGG TGGGGGAGG GCTGTCCACCT GTCCACTCAT
                                                                                   AP-2
-456   TATCCAGCCC TCTTATTCT CTGCTTCAGT CTGCTTCCAGT CTGCTTCAGT AGGGAGGG AGTGGAGTGG GAGACCTAGG GGTGGGGCTTC CCGACTTGC
-356   TGTACAGGAC CTCGACTAG CCAGGAGTG GTTGCCCTGA CACGTTAGTT GGGAGGCC GGCTAAAACT AGAGCCCAGG GGCCCCAAGT TCCAGACTGC
                                                              AP-2
-256   CCCTCCCCCC TCCCCGGAG CCAGGAGTG GTTGGTGAAA AGCTGGAGAA CAAACGGGTA GTCAGGGGGT TGAGCGATTA GAGCCCTTGT
                                                              SP1                                      SP1
-156   ACCTACCCA GGGGCCGG GGAATGGTTG GGGAGGAGGA GGAAGAGGTA GAGGGTAGGG CGCCAGGGGG GTTTTGTCA CCTGTCACCT GCTCGGCTG TGCCTAGGC
        SP1  SP1
+56    GGAGTGGGG GACCGGTATA AAGCGGTAGG CGCCTGTGCC CTCAAGCAGC CGCCAGCAGC CAGCGCCTGC CTGAATCTGT TCTGCCCCT
+45    CCCCACCCAT TTCACCACCA CCATG
```

CTGGAAAGTC CGGCTGGGGC GGGGACTGTG GGTTTCAGGG TAGAACTGCG TGTGGAACGG  60

GACAGGGAGC GGTTAGAAGG GTGGGGCTAT TCCGGGAAGT GGTGGGGGGA GGGA  114

FIG. 6

```
GCTTCCGTGC GCCTAGAGCG CAGCCTGCGA CTGCGGGACC CAACAACCAC GTGCTGCCGC    60
GGCCTGGGAT AGCTTCCTCC CCTCTGGCAC TGCTGCCGCA CACACCTCTT GGCTGTCGCG   120
CATTACGCAC CTCACGTGTG CTTTTGCCCC CGCCTACGTG CCTACCTGTC CCCAATACCA   180
CTCTGCTCCC CAAAGGATAG TTCTGTGTCC GTAAATCCCA TTCTGTCACC CCACCTACTC   240
TCTGCCCCCC CCTTTTTTGT TTTGAGACGG AGTCTTGCTC TGTCGCCCAG GCTGGAGTGC   300
AATGGCGCGA TCTCGGCTCA CTGCAACCTC CGCCTCCCGG GTTCAAGCGA TTCTCCTGCC   360
TCAGCCTCCT GAGTAGCTGG GGTTACAGCG CCCGCCACCA CGCTCGGCTA ATTTTTGTAG   420
TTTTTAGTAG AGACGAGGTT TCACCATCTT GGCCAGGCTG GTCTTGAACC CCTGACCTTG   480
TGATCCACTC GCCTCGGCCT TCCAAAGTGT TGGGATTACG GGCGTGACGA CCGTGCCACG   540
CCCGATCTGC CTCTTAAGTA CATAACGGCC CACACAGAAC GTGTCCAACT CCCCCGCCCA   600
CGTTCCAACG TCCTCTCCCA CATACCTCGG TGCCCCTTCC ACATACCTCA GGACCCCACC   660
CGCTTAGCTC CATTTCCTCC AGACGCCACC ACCACGCGTC CCGGAGTGCC CCCTCCTAAA   720
GCTCCCAGCC GTCCACCATG CTGTGCGTTC CTCCCTCCCT GGCCACGGCA GTGACCCTTC   780
TCTCCCGGGC CCTGCTTCCC TCTCGCGGGC TCTCGCTGCC TCACTTAAGC AGCGCTGCCC   840
TTACTCCTCT CCGCCCGGTC CGAGCGGCCC CTCAGCTTGC GCGGCCCAGC CCCGCAAGGC   900
TCCCGGTGAC CACTAGAGGG CGGGAGGAGC TCCTGGCCAG TGGTGGAGAG TGGCAAGGAA   960
GGACCCTAGG GTTCATCGGA GCCCAGGTTT ACTCCCTTAA GTGGAAATTT CTTCCCCCAC  1020
TCCCTCCTTG GCTTTCTCCA AGGAGGGAAC CCAGGCTGCT GGAAAGTCCG GCTGGGGCGG  1080
GGACTGTGGG TTTCAGGGTA GAACTGCGTG TGGAACGGGA CAGGGAGCGG TTAGAAGGGT  1140
GGGGCTATTC CGGGAAGTGG TGGGGGGAGG GAGCCCAAAA CTAGCACCTA GTCCACTCAT  1200
TATCCAGCCC TCTTATTTCT CGGCCCCGCT CTGCTTCAGT GGACCCGGGG AGGGCGGGGA  1260
AGTGGAGTGG GAGACCTAGG GGTGGGCTTC CCGACCTTGC TGTACAGGAC CTCGACCTAG  1320
CTGGCTTTCT TCCCCATCCC CACGTTAGTT GTTGCCCTGA GGCTAAAACT AGAGCCCAGG  1380
GGCCCAAGT TCCAGACTGC CCCTCCCCCC TCCCCGGAG CCAGGGAGTG GTTGGTGAAA   1440
GGGGGAGGCC AGCTGGAGAA CAAACGGGTA GTCAGGGGGT TGAGCGATTA GAGCCCTTGT  1500
ACCCTACCCA GGAATGGTTG GGGAGGAGGA GGAAGAGGTA GGAGGTAGGG GAGGGGCGG   1560
GGTTTTGTCA CCTGTCACCT GCTCCGGCTG TGCCTAGGGC GGGCGGGCGG GGAGTGGGGG  1620
GACCGGTATA AAGCGGTAGG CGCCTGTGCC CGCTCC                           1656
```

FIG. 7

ENHANCER SEQUENCE FOR MODULATING EXPRESSION IN EPITHELIAL CELLS

This is a divisional of application Ser. No. 08/324,465, filed on Oct. 17, 1994, now U.S. Pat. No. 5,565,334, which is a file-wrapper-continuation of U.S application Ser. No. 07/999,742, filed Dec. 31, 1992, now abandoned.

The work described herein was supported in part by United States Public Health Service Grant CA-38879 from the National Cancer Institute, and by a grant from the Department of Health and Human Services. The United States Government therefore has certain rights in the invention.

The invention relates to tissue-specific enhancer DNA sequences, which modulate the expression of downstream sequences in eukaryotic cells.

BACKGROUND OF THE INVENTION

Epithelium is the tissue that covers and lines the free surfaces of the body, and includes cells of the skin and sensory organs, as well as the specialized cells lining the blood vessels, gastrointestinal tract, air passages, ducts of the kidneys and endocrine organs. Epithelial cells maintain many diverse and essential cellular functions, including synthesizing and secreting proteins and other products, providing barriers, and proliferating to replace constantly eroded surface epithelia. Carcinomas, which are cancers derived from epithelial cells, account for the majority of malignant neoplasias, including most cancers of the breast, lung, colon, prostate, ovary, and pancreas.

The so-called DF3 gene encodes a high molecular weight glycoprotein which is aberrantly expressed by malignant human epithelia of various types. The DF3 glycoprotein is a member of a family of related carcinoma-associated antigens with core proteins ranging from 160 to 230 kD (Abe et al., J. Immunol. 139:257–261, 1987; Abe et al., Cancer Res. 49:2834–2839, 1989). This antigen is expressed on the apical borders of secretory mammary epithelium and at high levels in the cytosol of less differentiated malignant cells (Kufe et al., Hybridoma 3:223–232, 1984). DF3 antigen expression correlates with the degree of breast tumor differentiation (Lundy et al., Breast Cancer Res. Treat. 5:269–276,. 1985). Moreover, the detection of this antigen in human milk (Abe et al., Cancer Res. 44:4574–4577, 1984) has suggested that its expression represents a differentiated function of normal mammary cells.

Previous studies have demonstrated that the DF3 gene is highly over-expressed in human breast carcinomas and that expression of this gene is regulated at the transcriptional level (Kufe et al., Hybridoma 3:223–232, 1984; Abe et al., J. Cell. Physiol. 143:226–231, 1990).

SUMMARY OF THE INVENTION

Applicants have determined that the regulatory sequences for the DF3 gene, which is selectively expressed only in epithelial cells, are located in the 5'-flanking region of this gene; that a novel cis-acting enhancer sequence functions to control transcription in cells expressing this gene; and that this enhancer can be linked to a heterologous coding sequence to increase tissue-specific expression of that coding sequence in epithelium, and particularly in carcinoma cells.

As disclosed herein, the DF3 enhancer has been cloned and sequenced. By DF3 enhancer is meant either the sequence of SEQ ID NO:2, or a fragment thereof with enhancer activity. In preferred embodiments, the enhancer of the invention includes a sequence substantially identical to SEQ ID NO:1. In other preferred embodiments, the sequence is substantially identical to either the first 11 base pairs (SEQ ID NO:3) or the last 21 base pairs (SEQ ID NO:4) of SEQ ID NO:1. Enhancer activity can be determined by inserting the sequence to be evaluated into a chloramphenicol acetyltransferase (CAT) expression vector, transiently transfecting appropriate cells with the vector, and measuring CAT activity in the cells. Fragments which have enhancer activity cause transfected cells to express at least 25% of the CAT activity expressed by cells transfected with the CAT expression vector containing SEQ ID NO:2 as the enhancer sequence. This procedure is described in detail below.

One embodiment of the invention provides DNA, for example isolated DNA, which includes the DF3 enhancer, but does not encode DF3. "Isolated DNA" containing the DF3 enhancer refers to a segment of DNA that includes the DF3 enhancer, but which is free of the genes that, in the naturally-occurring genome of the organism from which the segment is derived, flank the DF3 gene. The isolated DNA, therefore, is not immediately contiguous with both of the coding sequences with which it is immediately contiguous (i.e., one at the 5' end and one at the 3' end) in the naturally-occurring genome of the organism from which the DNA of the invention is derived. The term includes, for example, a recombinant DNA which is incorporated into a vector; into an autonomously replicating plasmid or virus; or into the genomic DNA of a prokaryote or eukaryote, or which exists as a separate molecule (e.g., a cDNA or a genomic DNA fragment produced by PCR or restriction endonuclease treatment) independent of other DNA sequences.

Another aspect of the invention involves DNA containing DF3 enhancer and a DNA sequence (e.g., an antisense oligomer) which is antisense to a given naturally occurring mRNA encoding a naturally occurring polypeptide, which polypeptide is not DF3. An antisense oligomer is a short (generally at least 14 bp, and up to 100 or more bp) nucleotide sequence formulated to be complementary to a portion of a specific mRNA sequence. It is preferably located downstream from the enhancer of the invention and a functional promoter sequence, such as that of the HSV thymidine kinase gene; a poly A tail is typically located at the end of the antisense sequence to signal the end of the sequence. Standard methods relating to antisense technology have been described (Melani et al., Cancer Res. 51:2897–2901, 1991.) Following transcription of the antisense sequence into RNA, the antisense RNA binds to its target mRNA molecules within a cell, thereby inhibiting translation of the mRNA and down-regulating expression of the protein encoded by the mRNA. If, for example, the gene product of the target sequence stimulates tumor growth, down-regulation of the gene after antisense binding will result in suppression of tumor growth. Intended antisense oligodeoxynucleotides with antiproliferative activity, suitable for treatment of carcinomatous cells, include sequences antisense to N-myc in neuroectodermal cells (Whitesell et al., Mol. Cell. Biol. 11:1360–1370, 1991), c-myb for treatment of colon adenocarcinoma (Melani et al., Cancer Res. 51:2897–2901, 1991), type 1 regulatory subunit of the cAMP receptor protein kinase in breast, colon, and gastric carcinoma cells (Szczylik et al., Science 253:562–568, 1991), and K-ras proto-oncogene in small cell lung cancer lines (Vleminck et al., Cell 66:107–119, 1991).

Also provided is isolated DNA which contains the DF3 enhancer and a sequence encoding a heterologous polypeptide. A heterologous polypeptide is herein defined as any polypeptide other than DF3. The isolated DNA may include a nucleotide sequence substantially identical to that of SEQ ID NO:1, as shown in FIG. 6. In other embodiments, the isolated DNA contains either the first 11 base pairs or the last 21 base pairs of SEQ ID NO:1, or both. In another embodiment of the invention, the isolated DNA includes a nucleotide sequence substantially identical to that of SEQ ID NO:2, as shown in FIG. 7. The invention includes variations on the enhancer sequences shown which are at least 80% identical, and preferably at least 90% identical, to the naturally-occurring sequences given in the figures, and which function as enhancers of expression in carcinoma cells.

The isolated DNA of the invention may also include a radiation-inducible element. Preferably, the radiation-inducible element comprises a radiation-responsive enhancer-promoter, such as a CArG domain of an Egr-1 promoter, a TNF-A promoter, or a c-Jun promoter. These elements have been described in Weichselbaum et al., U.S. application Ser. No. 07/633,626, filed Dec. 20, 1990, the specification of which is herein incorporated by reference.

The heterologous polypeptide encoded by the DNA of the invention may be a cytotoxic polypeptide. Intended polypeptides include, but are not limited to, an enzymatically active subunit of a toxin such as Pseudomonas exotoxin A, diphtheria toxin, Shiga toxin, Shiga-like toxin, *E. coli* LT, C3 toxin, pertussis toxin, tetanus toxin, cholera toxin, or botulism toxin, or another cytotoxic polypeptide such as gelonin, ricin, or tumor necrosis factor. Other possible heterologous polypeptides include but are not limited to cAMP receptor polypeptide kinase, platelet factor 4, monocyte chemoattractants, herpes virus thymidine kinase, cytosine deaminase, WTp53, retinoblastoma protein, E-cadherin, fibronectin receptor, monocyte chemoattractant protein-I, interleukin-2, and interleukin-4.

The DNA or isolated DNA of the invention may be introduced into target cells by standard vectors and/or gene delivery systems. Suitable gene delivery systems may include liposomes, receptor-mediated delivery systems, naked DNA, and viral vectors such as herpes viruses, retroviruses, and adenoviruses, among others. Standard methods for transfecting cells with isolated DNA are well known to those skilled in the art of molecular biology.

The invention also includes cells transfected with the DNA of the invention. Preferably, the cells are epithelial cells (e.g., carcinoma cells), and they express a heterologous polypeptide encoded by the DNA of the invention.

A therapeutic composition is provided which includes a pharmaceutically acceptable carrier and a therapeutically effective amount of a nucleic acid, wherein the nucleic acid includes the DF3 enhancer operatively linked to a sequence encoding a heterologous polypeptide, to generate high-level expression of the polypeptide in epithelial cells transfected with the nucleic acid. By "operatively linked" it is meant that the enhancer is located sufficiently close to the coding sequence that it functions to enhance expression in an epithelial cell. For example, the enhancer may be located immediately upstream of the coding sequence start site, or up to approximately 500 bp upstream of the start site. It may alternatively be located downstream from the 3' end of the coding sequence, or within an intron between two exons of the coding sequence. The enhancer sequence may be inverse to the orientation observed in the naturally-occurring DF3 gene. Two or more copies of the DF3 enhancer may be arranged in tandem to increase expression of the heterologous protein to even higher levels. When the DF3 enhancer is arranged in tandem with a different tissue-specific enhancer, expression in multiple tissue types can be simultaneously enhanced. Likewise, two or more antisense or coding sequences can be arranged in tandem in the DF3-enhancer-containing DNA of the invention; expression of both of these sequences would be increased in epithelial cells, and especially in carcinoma cells. The therapeutic composition may also include a gene delivery system as described above. Pharmaceutically acceptable carriers are biologically compatible vehicles which are suitable for administration to an animal: e.g., physiological saline. A therapeutically effective amount is an amount of the DNA of the invention which is capable of producing a medically desirable result in a treated animal.

The invention provides a method for treating an animal with a carcinoma, by identifying the carcinoma-bearing animal and treating the animal with the therapeutic composition of the invention. This method may be used to treat any type of carcinoma, including but not limited to adenocarcinoma, adrenal carcinoma, basal cell carcinoma, brain carcinoma, ovarian carcinoma, breast carcinoma, colon carcinoma, pancreatic carcinoma, gastric carcinoma, hepatic carcinoma, biliary system carcinoma, skin cell carcinoma, reproductive tract carcinoma, urinary organ carcinoma, small cell carcinoma, squamous-cell carcinoma, undifferentiated carcinoma, and pulmonary carcinoma. In this list, where a neoplasm is designated by organ association, as in "ovarian carcinoma" or "pulmonary carcinoma", any carcinoma located in or immediately adjacent to the organ is included, without regard to whether the carcinoma is primary or is a metastasis from another location.

In addition, the invention provides a method of treating an animal with a metabolic disorder, by administering the therapeutic composition of the invention, where the heterologous polypeptide encoded by the DNA alleviates symptoms of the metabolic disorder. This method would be useful for treatment of various metabolic diseases characterized by the absence or reduced amount of a gene product (such as phenylalanine hydroxylase resulting in classic phenylketonuria, cystic fibrosis transmembrane regulator in cystic fibrosis, or Factor VIII or IX in hemophilia), or by structurally altered genes which are functionally inactive, as with $alpha_1$ antitrypsin in emphysema. The heterologous polypeptide encoded by the DNA in the therapeutic composition would correspond to the missing or malfunctioning gene product, e.g. phenylalanine hydroxylase, the CF gene product, Factor VIII, or $alpha_1$ antitrypsin.

Animals intended to be treated with the methods of the invention include any mammals to which the compounds of the invention may be administered, and in which the enhancer of the invention is functional. Animals specifically intended for treatment with the compounds and methods of the invention include humans, nonhuman primates, sheep, horses, cattle, pigs, goats, dogs, cats, rabbits, guinea pigs, hamsters, gerbils, rats and mice, as well as organs, tumors and cells derived or originating from these hosts.

The invention also includes a method of producing a polypeptide in vitro by culturing a cell of epithelial origin which has been transfected with the DNA of the invention, under conditions which facilitate the expression of the heterologous polypeptides encoded by the transgene. The polypeptides can then be isolated and purified by standard means.

Selective killing of cells and tumors is also encompassed by the invention. In this case, cytotoxic polypeptides expressed by the transfected cells act to kill the cells, or cells in the immediate vicinity of the transfected cells. In another embodiment, the transgene also encompasses, besides the DF3 enhancer and a sequence encoding the cytotoxic polypeptide, a radiation-inducible element. In this case, targeted radiation directed at a tumor, either in vitro or in situ in an animal, induces expression of a cytotoxic polypeptide only in those transfected cells which are of epithelial origin and which are irradiated. The heterologous polypeptide may also be one that, when secreted by the transfected cells, is capable of recruiting the organism's natural immunological defenses to attack cells in the vicinity of the transfected cells.

The invention further provides a vaccine, and a method of vaccinating an animal, wherein the heterologous polypeptide associated with the DF3 enhancer includes an antigenic determinant of an infectious organism. Appropriate organisms might include bacteria, viruses, protozoa, or helminths. For example, antigenic determinants of those pathogens which cause acquired immune deficiency syndrome (AIDS), polio, typhoid, cholera, and various enteric diarrheal diseases could be expressed and secreted by transfected epithelial cells lining the gastrointestinal tract, and thereby confer immunity to infection by both local and systemic immunological mechanisms. Useful antigens include the B subunit of cholera toxin (Mekalanos et al., Nature 306:551–557, 1983); the B subunit of Shiga toxin/Shiga-like toxin I (Calderwood et al., Proc. Natl. Acad. Sci. USA 84:4364–4368, 1987) or an antigenic peptide thereof (Harari et al., Infect. Immun. 56:1618–1624, 1988; Harari et al., Mol. Immunol. 27:613–621, 1990); an antigenic, enzymatically inactive mutant of diphtheria toxin (e.g., a deletion mutant lacking the A subunit portion of the toxin, or having an inactivating mutation in the A subunit); an antigenic, enzymatically inactive mutant of pertussis toxin, tetanus toxin, or E. coli LT; or a viral capsid polypeptide. Immunity to respiratory infections would result from transfection of lung epithelial cells with the appropriate DNA of the invention. Similar immunization would be useful in vaccinating animals against various diseases of veterinary importance, including many parasitic diseases such as toxocariasis, filariasis, coccidiosis, strongyloidiasis, and cestodiasis. The specialized ability of epithelial cells to produce and secrete proteins makes them particularly suitable targets for DNA-based vaccines.

In a further embodiment of the invention, epithelial cells within an animal are transfected with DNA which includes the DF3 enhancer and a sequence encoding a polypeptide which confers resistance to the effects of a chemotherapeutic drug. In a preferred example, the polypeptide encodes P-glycoprotein, the product of the multidrug resistance (MDR-1) gene. Cells which express this glycoprotein have a highly enhanced membrane transport pump, which quickly clears the cells of many common chemotherapeutic drugs, including vinca alkaloids, anthracyclines, epipodophyllotoxins, L-asparaginase, colchicine, and other antineoplastic antibiotics. Another polypeptide which might be beneficially expressed by transfected epithelial cells is dihydrofolate reductase, the expression of which would protect transfected cells from the toxic effects of methotrexate. Such expression in epithelial cells of a cancer patient would protect the transgenic cells from the effects of chemotherapeutics administered to treat non-carcinomatous neoplasms in the patient, without affecting the efficacy of the chemotherapeutics against the non-carcinomatous neoplasm itself. The patient would then be spared the often life-threatening side effects of chemotherapy, such as gastrointestinal injury, which result from epithelial cell damage. In addition, protection of the epithelial cells would allow higher doses of chemotherapeutic drugs to be administered, with potentially better clinical outcomes. In another embodiment of this method, cells of the gastrointestinal tract could be protected by transfecting these cells with an orally-administered vector; nongastrointestinal malignancies, including carcinomatous and noncarcinomatous neoplasms, could then be treated with systemic chemotherapeutics with minimal effect on the gastrointestinal epithelial cells.

Another aspect of the invention includes a transgenic animal, the genome of which contains a transgene including DF3 enhancer operatively linked to a sequence encoding a heterologous polypeptide. Detailed methods for producing these animals are presented in U.S. Pat. No. 4,736,866, the specification of which is hereby incorporated by reference. The intended transgenic animals may be of any nonhuman mammalian or avian species, but preferably include nonhuman primates, sheep, horses, cattle, pigs, goats, dogs, cats, rabbits, chickens, and rodents such as guinea pigs, hamsters, gerbils, rats, and mice.

The compounds and compositions of the invention may be administered by any medically acceptable method. Suitable methods include injections, by parenteral routes such as intravenous, subcutaneous, intramuscular, intratumor, intraperitoneal, intraventricular, intraepidural, or others, as well as oral, nasal, transdermal, transmucosal, ophthalmic, rectal, or topical routes. The compounds may also be applied directly to exposed tissue surfaces, such as during a surgical procedure. In addition, the compounds of the invention are suitable for inhalant administration, for example as a nebulized or aerosolized preparation.

As is well known in the medical arts, dosages for any one patient depends upon many factors, including the patient's size, body surface area, age, the particular compound to be administered, sex, time and route of administration, general health, and other drugs being administered concurrently. Dosages for the compounds of the invention will vary, but a preferred dosage for oral or inhaled administration to a patient is from $10^5$ to $10^{20}$ copies of a DNA molecule of the invention, as specified above. A patient receiving intravenous vector preparations may be infused with from approximately $10^6$ to $10^{22}$ copies of the vector.

Other features and advantages of the invention will be apparent from the following description and from the claims.

BRIEF DESCRIPTION OF THE DRAWINGS

FIG. 1A (SEQ ID NO:5) is a representation of the nucleotide sequence of the 5'-flanking region of the DF3 gene, plus the first 70 nucleotides of coding sequence. The transcription start site is indicated by the arrow. Potential binding sites with complete homology to the indicated cis-elements are highlighted by boxes.

(A) f(−507/−483) (CCGGGAAGTGGTGGGGGGAGGGAGC) (SEQ ID NO:6) was end-labeled and incubated with 10 Ag MCF-7 nuclear proteins. Unlabeled f(−507/−483) and f(−611/−579) were added at a 50- or 250-fold molar excess compared to the labeled probe. The unlabeled oligonucleotide corresponding to the consensus sequence for SP1 was added at a 50-fold molar excess.

(B) f(−507/−483) and a mutated fragment at positions −496 and −495 (CCGGGAAGTGGCGAGGGG GAGGGAGC) (SEQ ID NO:7) were end-labeled (both 1×10$^5$ CPM, 5×10$^4$ CPM/ng) and incubated with MCF-7 nuclear proteins.

Figure 4:
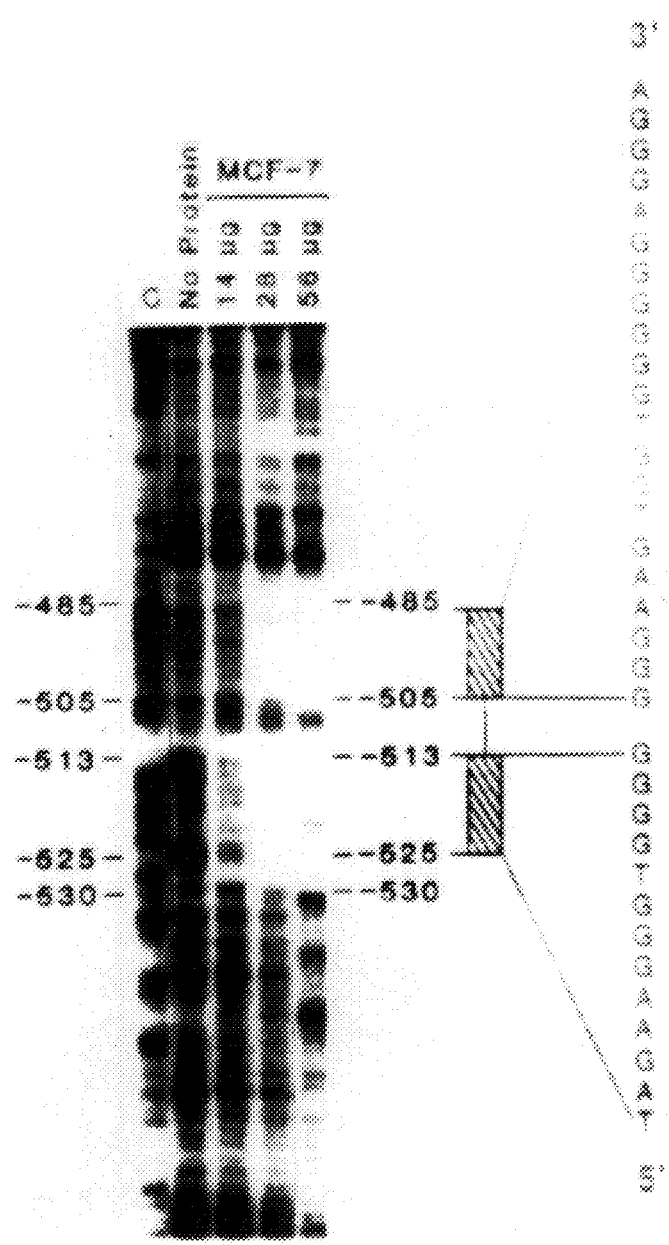

FIG. 4 is a DNase I analysis of protein binding to f(−618/−410). f(−618/−410) was end-labeled (1×10$^4$ CPM/ 0.1 ng) and incubated with the indicated amounts of MCF-7 nuclear proteins. The samples were subjected to DNase I digestion and analyzed in 12% polyacrylamide/urea gels. C represents analysis of cytosines as determined by Maxam-Gilbert sequencing. The hatched boxes reflect regions protected from DNase I digestion.

Figure 5:
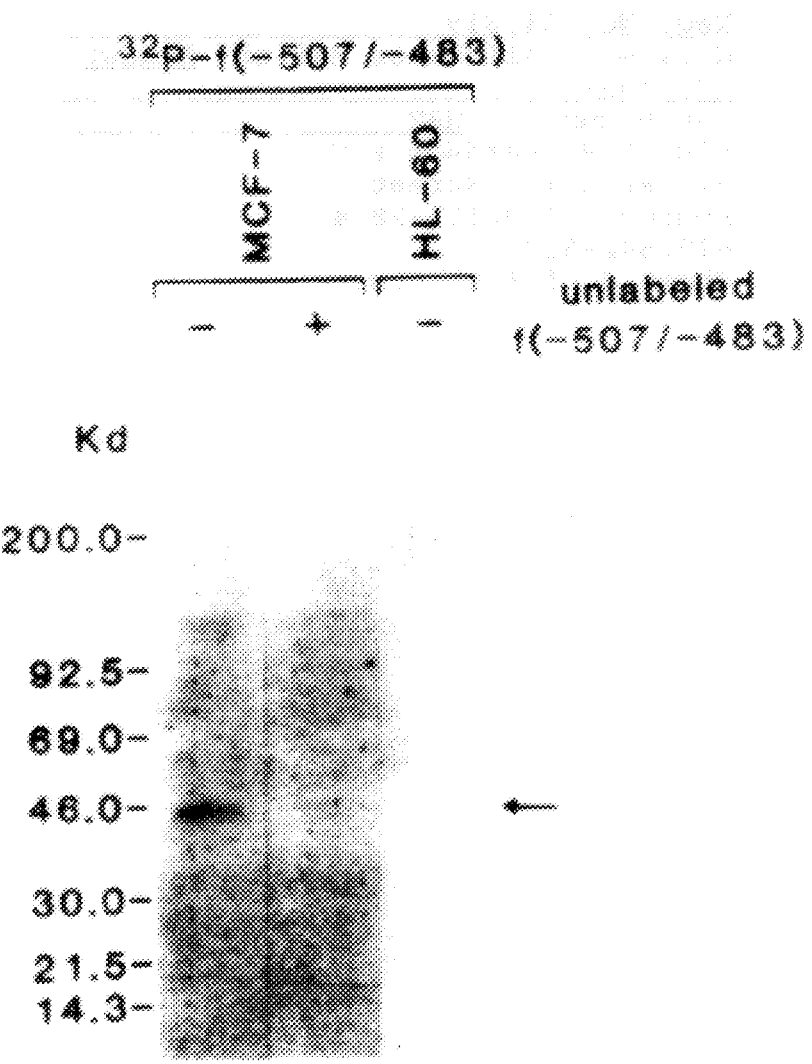

FIG. 5 is an autoradiogram of a gel illustrating f(−507/−483) interacting with a 45 kD nuclear protein in MCF-7 cells. Nuclear proteins (200 µg) from MCF-7 and HL-60 cells were separated by polyacrylamide gel electrophoresis and transferred to a nitrocellulose sheet. Lanes were incubated with $^{32}$P-f(−507/−483) in the absence or presence of a 100-fold molar excess of unlabeled fragment.

FIG. 6 is a representation of the nucleotide sequence of a functional region of the DF3 enhancer (SEQ ID NO: 1), which represents nucleotides −598 to −485 of the 5'-flanking region of the DF3 gene shown in FIG. 1A (SEQ ID NO: 5).

FIG. 7 (SEQ ID NO:2) is a representation of the nucleotide sequence of the DF3 5'-flanking sequence, as shown in FIG. 1A (SEQ ID NO:5), except without any of the DF3 coding sequence shown in FIG. 1A.

DETAILED DESCRIPTION

Cell culture. Human MCF-7 breast carcinoma cells (Michigan Cancer Foundation, Detroit, Mich.; American Type Culture Collection) were grown as a monolayer in Dulbecco's modified Eagle's medium (DMEM) with 10% heat-inactivated fetal bovine serum, 100 units/ml penicillin, 100 µg/ml streptomycin, 2 mM L-glutamine and 0.25 IU/ml insulin.

Plasmid construction

A pΔ vector was generated by excising the SV40 promoter and enhancer regions from pSVT7 (Bird et al., J. Cell. Biol. 105:2905–2914, 1987). Chloramphenicol acetyltransferase (CAT) expression vectors, pSVT7CAT and PΔCAT, were produced by inserting the CAT gene in the multicloning HindIII site of pSVT7 and pΔ, respectively. A p-1656CAT vector was constructed by inserting the XmnI fragment (positions −1656 to +31) of the DF3 gene into pΔCAT at the PstI site by blunt-ended DNA ligation. The p-725CAT vector was prepared by inserting the blunt-ended SstI/XmnI fragment (positions −725 to +31) into pΔCAT. A series of deletion vectors was generated from p-725CAT after treatment with SstI or XbaI and subsequent digestion with exonuclease III and S1 nuclease. Sequencing of the constructs was performed by dideoxy termination (Sanger et al., Proc. Natl. Acad. Sci. USA 74:5463–5467, 1977).

Reporter assays

All vectors used in the reporter assays were purified twice by cesium chloride gradient centrifugation and phenol-chloroform extraction. Twenty µg of each plasmid were transfected into 3×10$^5$ MCF-7 cells by the Ca$_2$PO$_4$ procedure (Davis et al., Basic Methods in Molecular Biology (Elsevier, N.Y.) pp. 285–289, 1986). The cells were incubated in complete medium for 48 hours after transfection, harvested and lysed in 0.25 M Tris-HCl (pH 8.0) by three cycles of freeze-thawing. CAT activity was assayed in 125 µl reactions containing 10 to 50 µl of cell extract, 125 nCi [$^{14}$C]chloramphenicol (DuPont Co., Boston, Mass.; 57 mCi/ mmol), 250 mM Tris-HCl, pH 8.0, and 25 µg n-butyryl coenzyme A (Sigma) for 1 hour at 37° C. The reaction was terminated by adding 300 µl xylene. The non-butyrated chloramphenicol was removed by washing twice with 100 µl of 0.25 M Tris-HCl (pH 8.0). The xylene layer containing the butyrated chloramphenicol was assayed by scintillation counting (Seed et al., Gene 67:271–277, 1988).

Electrophoretic mobility shift assays (EMBAs)

Nuclear proteins were prepared according to previously described methods (Dignam et al., Nucl. Acids. Res. 11:1475–1489, 1983). Synthetic oligonucleotides were end-labeled with the appropriate [α-$^{32}$P]dNTPs using DNA polymerase I (Klenow fragment) and purified by Nuc Trap columns (Stratagene, LaJolla, Calif.). Binding assays were performed as described (Henninghausen et al., Guide to Molecular Cloning Techniques, (Academic Press, N.Y.) pp. 721–735, 1987). Ten µg of nuclear proteins were incubated with 10 µg poly(dI-dC) in 25 µl of 10 mM Tris-HCl buffer (pH 7.5) containing 50 or 150 mM KCl, 5 mM MgCl$_2$, 1 MM DTT, 1 mM EDTA, 12.5% glycerol and 0.1% Triton X-100 for 30 min at room temperature. After adding the labeled probe (1×10$^5$ CPM, 1 ng) and incubating for an additional 30 min, the samples were separated in a low ionic strength 4.5% polyacrylamide gel containing 1 mM EDTA, 3.3 mM sodium acetate and 6.7 mM Tris- HCl (pH 7.5) or in a high ionic strength gel containing 50 mM Tris-HCl (pH 8.5), 380 mM glycine and 2 mM EDTA (Henninghausen et al., Guide to Molecular Cloning Techniques (Academic Press N.Y.) pp. 721–735, 1987; Staudt et al., Nature 323:640–643, 1986). Unlabeled oligonucleotides as competitors, including the consensus sequences of SP1, NF-1, AP-1, AP-2 and AP-3 (Stratagene), were added at the same time as the labeled fragment.

DNase I footprint analysis

Fragment f(−618/−410) (SEQ ID NO:8) was ligated into pGEM3 at the SmaI site. The vector was digested with EcoRI and AccI, end-labeled with $^{32}$P-dATP and dTTP at the EcoRI site and purified in a 5% native polyacrylamide gel. The specific activity of the labeled fragment was approximately 3×10$^5$ CPM/ng. The assay was performed as described (Jones et al., Cell 42:559–572, 1985). The reaction products were analyzed by 12% polyacrylamide/urea gel electrophoresis and subjected to autoradiography. Sequences were monitored by the Maxam-Gilbert procedure (Maxam et al., Methods in Enzymol. (Academic Press, N.Y.) 65:499–560, 1980).

Southwestern analysis

Nuclear proteins (200 μg) were prepared as described (Dignam et al., Nucl. Acids. Res. 11:1475–1489, 1983), separated by 3–15% SDS-polyacrylamide gel electrophoresis and transferred to a nitrocellulose sheet (Lammnli, Nature 227:680–695, 1970; Towbin et al., Proc. Natl. Acad. Sci. USA 76:4350–4355, 1979). The sheet was incubated in 10 mM Tris-HCl (pH 7.5) containing 5% skimmed milk and then in 10 mM Tris-HCl (pH 7.9) containing $^{32}$P-labeled oligonucleotide probe (106 CPM/ml), 50 mM NaCl, 10 mM $MgCl_2$, 0.1 mM EDTA, 1 mM DTT and 10 μg/ml poly(dI-dC) for 60 min at room temperature. The sheet was washed with the same buffer containing 200 mM NaCl and exposed to x-ray film (Patel et al., EMBO J. 2:137–142, 1983; Miskimins et al., Proc. Natl. Acad. Sci. USA 82:6741–6744, 1985).

RESULTS

Sequence of the DP3 5'-flanking region

A genomic library from MCF-7 cells was previously used to isolate a clone containing over 2 kb of sequences upstream to the DF3 transcription start site (Abe et al., Biochem. Biophys. Res. Commun. 165:644–649, 1989, herein incorporated by reference). Digestion of this clone with XmnI resulted in a fragment extending from positions −1656 to +31. The nucleotide sequence to position −1656 includes a potential TATA box (TATAAA) 25 bases upstream to the transcription start site (FIG. 1A). The 5' flanking region also includes potential binding sites with complete homology to the consensus sequences for SP1, AP-1, AP-2, AP-3, NF-1 and the estrogen receptor half-site (FIG. 1A).

Functional analysis of the putative DF3 promoter region

Figure 1B:
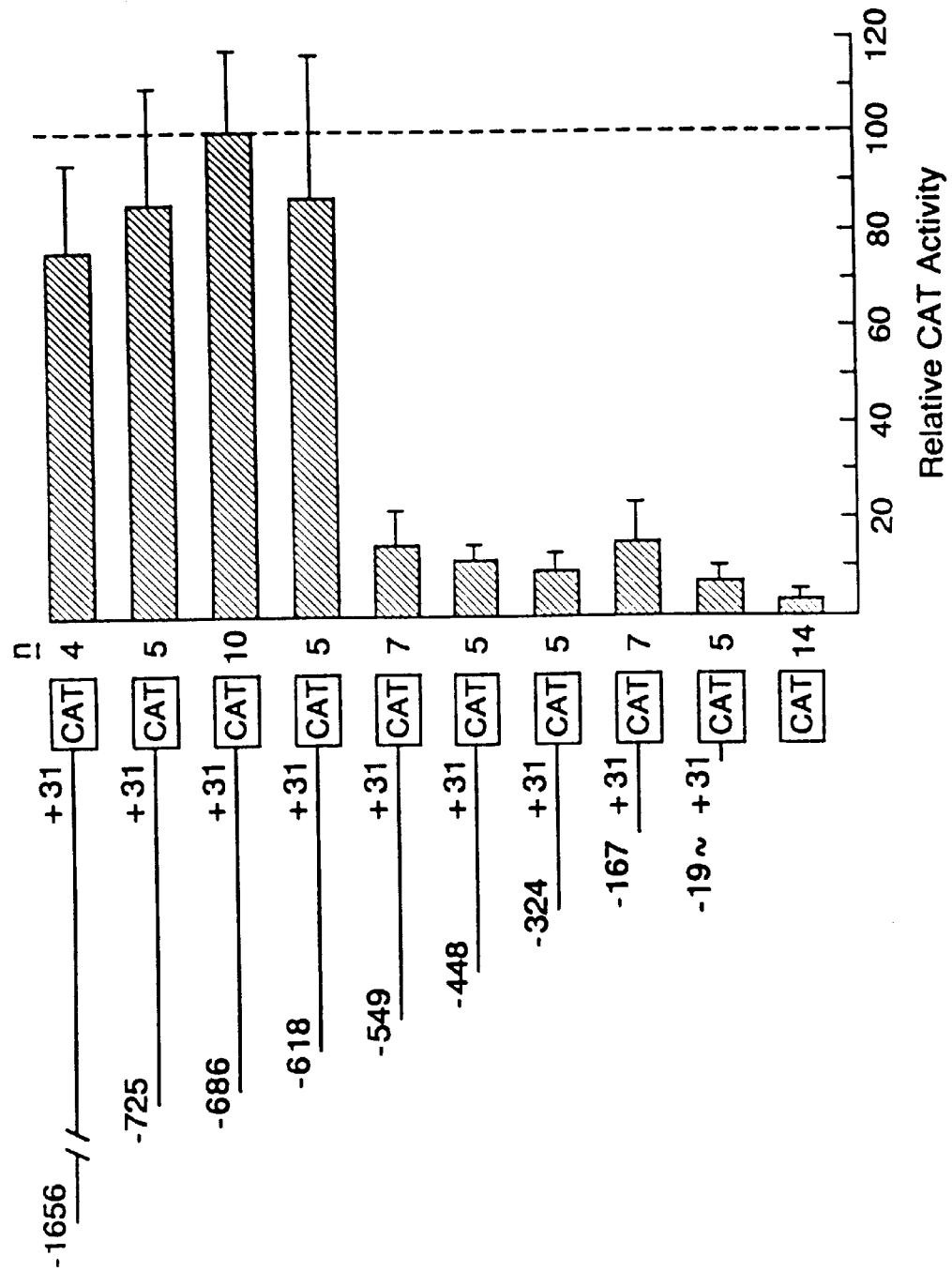
FIG. 1B is a transient expression analysis of DF3 promoter deletion constructs: MCF-7 cells were transfected with deleted promoter fragments linked to CAT. Relative CAT activities are expressed as values compared to that obtained with p-686CAT (assigned a value of 100). The results represent the mean±SD of the indicated number (n) of experiments.

A series of experiments confirmed that DF3 gene expression is regulated at the transcriptional level in MCF-7 cells. A series of 5' deleted DF3 promoter-CAT constructs were transfected into these cells to identify the functional cis-element(s). Transfection of plasmid p-1656CAT resulted in CAT activities that were approximately 25-fold higher than that obtained with pΔCAT (FIG. 1B). Similar levels of CAT activity were obtained with p-725CAT, p-686CAT and p-618CAT (FIG. 1B). In contrast, transfection of p-549CAT was associated with a decrease in transcriptional activity to approximately 15% of that found with p-686CAT. Moreover, transfection of the more extensively deleted constructs (p-448CAT, p-324CAT, p-167CAT) yielded levels of relative activity that were similar to those obtained with constructs containing a minimal promoter region (p-19CAT) (FIG. 1B). Taken together, these findings indicated that the sequence between positions −618 and −549 includes one or more elements involved in the control of DF3 gene transcription.

Figure 2A:
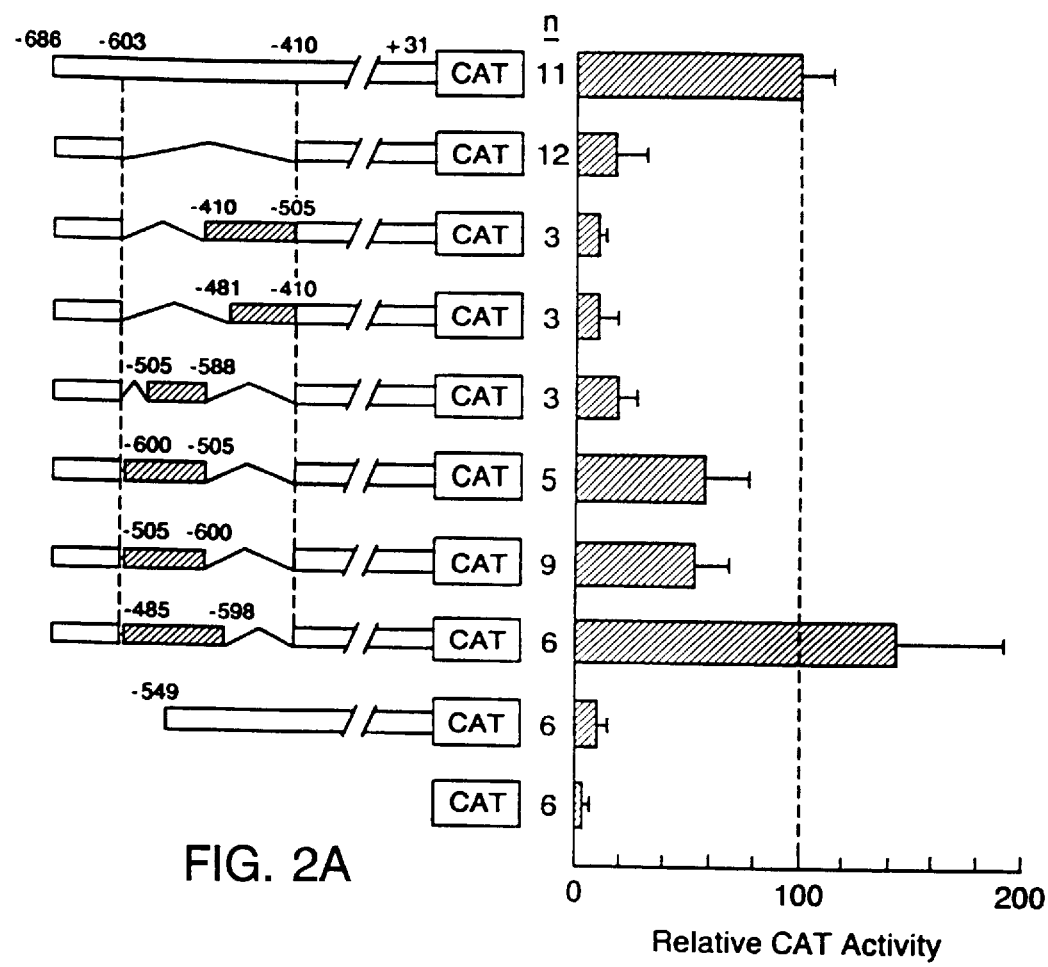
FIG. 2A is a transient expression analysis of p-686CAT internal deletion vectors: p-686CAT was digested with BstXI and SmaI to create a construct with deletion of the region from positions −603 to −410. Smaller fragments of f(−603/−410) were religated into the deleted region. Relative CAT activities are expressed as values compared to that obtained with p-686CAT. The results represent the mean±SD of the indicated number (n) of independent experiments.

In order to further define the functional element(s), a series of internal deletions was prepared using p-686CAT. Deletion of the region from positions −603 to −410 decreased (>80%) transcription of p-686CAT to a level approaching that obtained with p-549CAT (FIG. 2A). Similar findings were obtained with reinsertion of f(−410/−505) or f(−481/−410) (FIG. 2A). These results were thus in concert with the likelihood that the functional enhancer sequences were upstream to position −549 (FIG. 1B). However, ligation of f(−505/−588) into this cassette had little if any effect, while reinsertion of f(−600/−505) or f(−505/−600) resulted in only partial (54–60%) recovery of CAT activity (FIG. 2A). In contrast, f(−485/−598) conferred complete restitution of the activity obtained with p-686CAT (FIG. 2A). These results indicated that sequences within f(−598/−485) were responsible for control of DF3 gene transcription.

Figure 2B:
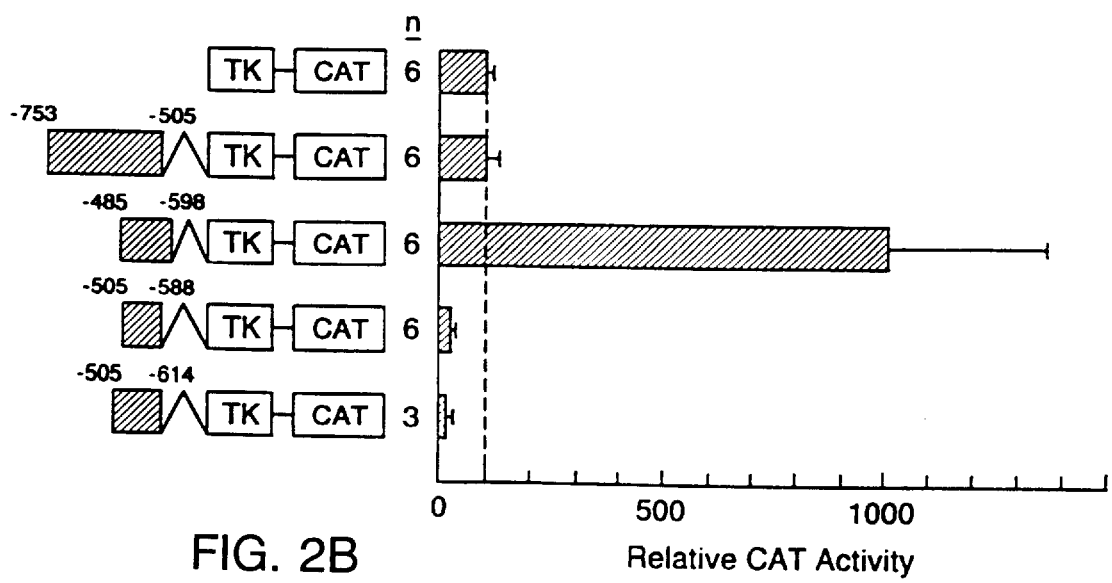
FIG. 2B is a transient expression analysis of heterologous promoter constructs: Fragments of the DF3 promoter were inserted upstream to the TK promoter in pBLCAT2. MCF-7 cells were transfected with the indicated constructs. The results (mean±SD) are expressed as reactive CAT activity compared to that obtained with TK-CAT (assigned a value of 100).

A heterologous promoter was used to determine the enhancing activities of sequences upstream to position −485. Single copies of fragments f(−753/−505), f(−485/−598), f(−505/−588) and f(−505/−614) were inserted upstream to the herpes simplex virus minimal thymidine kinase (TK) promoter in pBLCAT2 (FIG. 2B). CAT activity of PBL-CAT2 was normalized to 100. Insertion of f(−753/−505) into this vector had little if any effect, while f(−485/−598) enhanced TK promoter activity by over 10-fold (FIG. 2B). These results provided further support for the presence of functional elements between positions −598 and −485. Moreover, the finding that both f(−505/−588) and f(−505/−614) decreased the activity of pBLCAT2 (FIG. 2B) emphasized the importance of the sequence between −505 and −485.

Figures 3A, 3B:
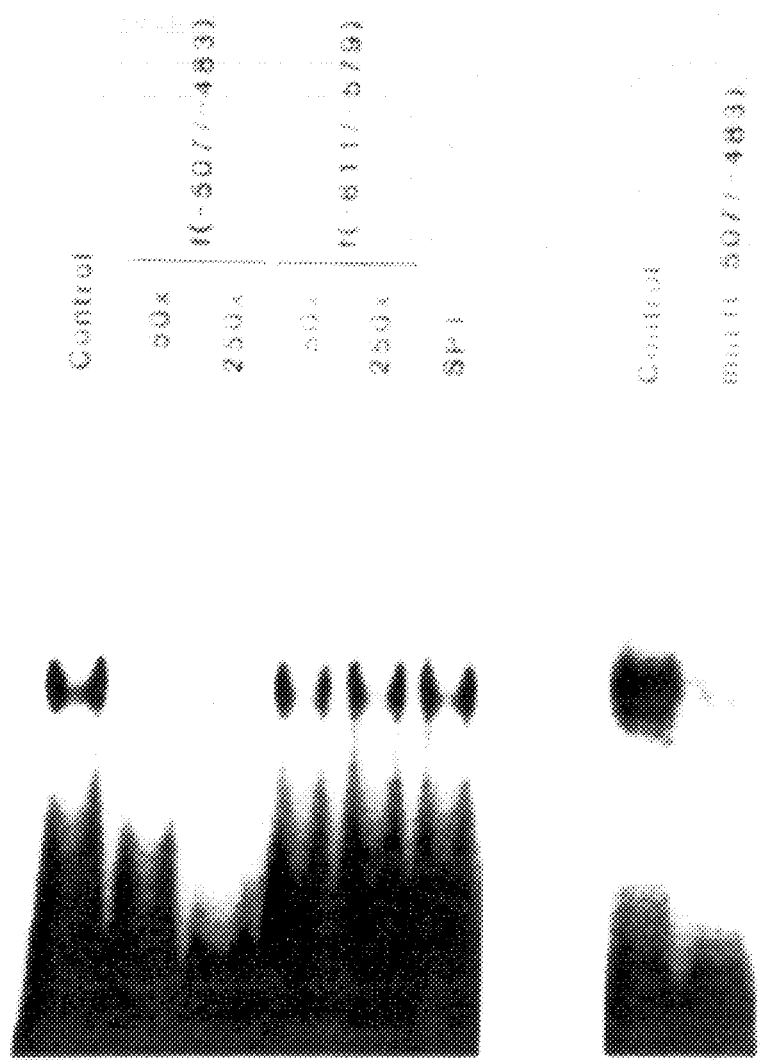
FIGS. 3A and B are gel retardation analyses of nucleoprotein complexes found with f(−507/−483)

Interaction of nuclear proteins with the DF3 promoter. The results of the reporter assays prompted further studies on the interaction of nuclear proteins with the putative regulatory regions of the DF3 promoter. EMSAs were performed with f(−507/−483). Incubation of end-labeled f(−507/−483) with nuclear proteins from MCF-7 cells resulted in a clearly detectable retarded fragment (FIG. 3A). In order to determine whether this complex reflected specific DNA-protein binding, unlabeled f(−507/−483) was added to the reaction. In these experiments, a 50-fold excess of unlabeled probe partially inhibited formation of the complex, while a 250-fold excess resulted in complete inhibition (FIG. 3A). In contrast, use of unlabeled f(−611/−579) as a competitor had no detectable effect (FIG. 3A). There was also no detectable inhibition of this complex when using unrelated oligonucleotides containing SP1, AP-1, AP-2, AP-3, or NF-1 sequences (FIG. 3A and data not shown). These findings, taken together with the absence of a detectable band when using nuclear proteins from HL-60 (DF3 antigen negative cells, data not shown), supported the formation of a specific f(−507/483)-MCF-7 nuclear protein complex. There was also no detectable complex formation when incubating labeled f(−515/−496) or f(−529/−510) with the MCF-7 nuclear proteins (data not shown). Finally, alterations in the sequence of f(−507/−483) at positions −496/−495 resulted in nearly complete inhibition of complex formation (FIG. 3B).

The interaction of nuclear proteins with the DF3 promoter was further addressed by DNaseI footprinting. End-labeled f(−618/−410) was incubated with increasing amounts of MCF-7 nuclear proteins and then subjected to digestion with DNase I. The demonstration that one protected region extended from positions −485 to −505 (FIG. 4) is in concert with the sequences identified by reporter and gel retardation assays. Another region extending from positions −513 to −525 was also protected by MCF-7 nuclear proteins (FIG. 4). Moreover, there was enhancement of sequences adjacent to the protected regions (at positions −506 to −510 and upstream to position −530) (FIG. 4).

Southwestern analysis was performed to identify the size of the protein(s) that interact with f(−507/−483). This fragment interacted with a species with an apparent molecular weight of 45 kd (FIG. 5). This interaction was inhibited by a 100-fold excess of unlabeled to labeled fragment. In contrast, there was no detectable interaction of f(−507/−483) with nuclear proteins from HL-60 cells (FIG. 5). Moreover, incubation of labeled f(−611/−579) with the MCF-7 nuclear proteins failed to demonstrate DNA-protein interaction (data not shown). Taken together, these results indicated that f(−507/−483) specifically interacts with a nuclear 45 kD protein.

Example

A patient is diagnosed with a malignant inoperable pulmonary carcinoma. Using standard methods, a genetic construct is prepared bearing the DF3 enhancer operably linked to the gene for herpes simplex-thymidine kinase (HS-tk). The HS-tk gene, when introduced into tumor cells, confers sensitivity to the anti-herpes drug gancyclovir. The construct is inserted into a retroviral vector, and 108 copies of the vector are injected into the tumor. Of all of the cells which may take up the vector, only the transfected carcinoma cells which naturally overexpress DF3 will highly overexpress the HS-tk transgene. The patient is then treated with gancyclovir, which acts primarily on those cells which overexpress HS-tk, causing the tumor to regress.

Other Embodiments

The invention includes the use of the DF3 enhancer to modulate expression of any protein which is either partially or wholly encoded in a location downstream to the DF3 enhancer. Also included are allelic variants, natural mutants, and induced mutants of the DF3 enhancer, which variants and mutants retain the ability to enhance expression in epithelial cells comparable to the level of enhancement produced by the sequence shown in SEQ ID NO:1.

Similar enhancers derived from corresponding genes in other mammalian species are included within the scope of the invention. Such enhancers may be identified by, for example, identifying the enhancer associated with a coding sequence from a particular mammalian species, which coding sequence hybridizes under stringent conditions with a probe consisting of a 20-nucleotide segment of the human DF3 coding sequence, and which encodes a polypeptide that is expressed predominantly in epithelial cells of that species. Alternatively, a probe consisting of a segment of the human DF3 enhancer can be used as a probe for a similar sequence in the genome or cDNA of another species. A sequence which functions as an epithelium-specific enhancer and which hybridizes with a probe containing the sequence of SEQ ID NO:1 or the sequence of SEQ ID NO:4, under the following hybridization conditions, would be within the invention: prehybridization in 50% formamide, 5X SSC, 25 mM potassium phosphate buffer (pH 7.4), 5X Denhardt's, and 50 µg/ml denatured salmon sperm DNA for 4–12 hours at 20° C.; hybridization for 12–24 hours at 20° C.; washing in 5X SSC containing 0.1% SDS, at 20° C.

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
( A ) LENGTH: 114
( B ) TYPE: nucleic acid
( C ) STRANDEDNESS: double
( D ) TOPOLOGY: linear ( x i ) SEQUENCE DESCRIPTION: SEQ ID NO: 1:

```
CTGGAAAGTC  CGGCTGGGGC  GGGGACTGTG  GGTTTCAGGG  TAGAACTGCG  TGTGGAACGG      60

GACAGGGAGC  GGTTAGAAGG  GTGGGGCTAT  TCCGGGAAGT  GGTGGGGGGA  GGGA          114
```

( 2 ) INFORMATION FOR SEQ ID NO: 2:

( i ) SEQUENCE CHARACTERISTICS:
( A ) LENGTH: 1656
( B ) TYPE: nucleic acid
( C ) STRANDEDNESS: double
( D ) TOPOLOGY: linear ( x i ) SEQUENCE DESCRIPTION: SEQ ID NO: 2:

```
GCTTCCGTGC  GCCTAGAGCG  CAGCCTGCGA  CTGCGGGACC  CAACAACCAC  GTGCTGCCGC      60

GGCCTGGGAT  AGCTTCCTCC  CCTCTGGCAC  TGCTGCCGCA  CACACCTCTT  GGCTGTCGCG    120

CATTACGCAC  CTCACGTGTG  CTTTTGCCCC  CGCCTACGTG  CCTACCTGTC  CCCAATACCA    180

CTCTGCTCCC  CAAAGGATAG  TTCTGTGTCC  GTAAATCCCA  TTCTGTCACC  CCACCTACTC    240

TCTGCCCCCC  CCTTTTTTGT  TTGAGACGG   AGTCTTGCTC  TGTCGCCCAG  GCTGGAGTGC    300

AATGGCGCGA  TCTCGGCTCA  CTGCAACCTC  CGCCTCCCGG  GTTCAAGCGA  TTCTCCTGCC    360

TCAGCCTCCT  GAGTAGCTGG  GGTTACAGCG  CCCGCCACCA  CGCTCGGCTA  ATTTTTGTAG    420

TTTTTAGTAG  AGACGAGGTT  TCACCATCTT  GGCCAGGCTG  GTCTTGAACC  CCTGACCTTG    480

TGATCCACTC  GCCTCGGCCT  TCCAAAGTGT  TGGGATTACG  GGCGTGACGA  CCGTGCCACG    540

CCCGATCTGC  CTCTTAAGTA  CATAACGGCC  CACACAGAAC  GTGTCCAACT  CCCCCGCCCA    600
```

-continued

| | | | | | |
|---|---|---|---|---|---|
| CGTTCCAACG | TCCTCTCCCA | CATACCTCGG | TGCCCCTTCC | ACATACCTCA | GGACCCCACC | 660
| CGCTTAGCTC | CATTTCCTCC | AGACGCCACC | ACCACGCGTC | CCGGAGTGCC | CCCTCCTAAA | 720
| GCTCCCAGCC | GTCCACCATG | CTGTGCGTTC | CTCCCTCCCT | GGCCACGGCA | GTGACCCTTC | 780
| TCTCCCGGGC | CCTGCTTCCC | TCTCGCGGGC | TCTCGCTGCC | TCACTTAAGC | AGCGCTGCCC | 840
| TTACTCCTCT | CCGCCCGGTC | CGAGCGGCCC | CTCAGCTTGC | GCGGCCCAGC | CCCGCAAGGC | 900
| TCCCGGTGAC | CACTAGAGGG | CGGGAGGAGC | TCCTGGCCAG | TGGTGGAGAG | TGGCAAGGAA | 960
| GGACCCTAGG | GTTCATCGGA | GCCCAGGTTT | ACTCCCTTAA | GTGGAAATTT | CTTCCCCCAC | 1020
| TCCCTCCTTG | GCTTTCTCCA | AGGAGGGAAC | CCAGGCTGCT | GGAAAGTCCG | GCTGGGGCGG | 1080
| GGACTGTGGG | TTTCAGGGTA | GAACTGCGTG | TGGAACGGGA | CAGGGAGCGG | TTAGAAGGGT | 1140
| GGGGCTATTC | CGGGAAGTGG | TGGGGGGAGG | GAGCCCAAAA | CTAGCACCTA | GTCCACTCAT | 1200
| TATCCAGCCC | TCTTATTTCT | CGGCCCCGCT | CTGCTTCAGT | GGACCCGGGG | AGGGCGGGGA | 1260
| AGTGGAGTGG | GAGACCTAGG | GGTGGGCTTC | CCGACCTTGC | TGTACAGGAC | CTCGACCTAG | 1320
| CTGGCTTTCT | TCCCCATCCC | CACGTTAGTT | GTTGCCCTGA | GGCTAAAACT | AGAGCCCAGG | 1380
| GGCCCCAAGT | TCCAGACTGC | CCCTCCCCCC | TCCCCGGAG | CCAGGGAGTG | GTTGGTGAAA | 1440
| GGGGGAGGCC | AGCTGGAGAA | CAAACGGGTA | GTCAGGGGT | TGAGCGATTA | GAGCCCTTGT | 1500
| ACCCTACCCA | GGAATGGTTG | GGGAGGAGGA | GGAAGAGGTA | GGAGGTAGGG | GAGGGGGCGG | 1560
| GGTTTTGTCA | CCTGTCACCT | GCTCCGGCTG | TGCCTAGGGC | GGGCGGGCGG | GGAGTGGGGG | 1620
| GACCGGTATA | AAGCGGTAGG | CGCCTGTGCC | CGCTCC | | | 1656

(2) INFORMATION FOR SEQ ID NO: 3:

(i) SEQUENCE CHARACTERISTICS:
        (A) LENGTH: 11
        (B) TYPE: nucleic acid
        (C) STRANDEDNESS: double
        (D) TOPOLOGY: linear (xi) SEQUENCE DESCRIPTION: SEQ ID NO: 3:

CTGGAAAGTC C    11

(2) INFORMATION FOR SEQ ID NO: 4:

(i) SEQUENCE CHARACTERISTICS:
        (A) LENGTH: 21
        (B) TYPE: nucleic acid
        (C) STRANDEDNESS: double
        (D) TOPOLOGY: linear (xi) SEQUENCE DESCRIPTION: SEQ ID NO: 4:

GGGAAGTGGT GGGGGGAGGG A    21

(2) INFORMATION FOR SEQ ID NO: 5:

(i) SEQUENCE CHARACTERISTICS:
        (A) LENGTH: 1725
        (B) TYPE: nucleic acid
        (C) STRANDEDNESS: double
        (D) TOPOLOGY: linear (xi) SEQUENCE DESCRIPTION: SEQ ID NO: 5:

| | | | | | |
|---|---|---|---|---|---|
| GCTTCCGTGC | GCCTAGAGCG | CAGCCTGCGA | CTGCGGGACC | CAACAACCAC | GTGCTGCCGC | 60
| GGCCTGGGAT | AGCTTCCTCC | CCTCTGGCAC | TGCTGCCGCA | CACACCTCTT | GGCTGTCGCG | 120
| CATTACGCAC | CTCACGTGTG | CTTTTGCCCC | CGCCTACGTG | CCTACCTGTC | CCCAATACCA | 180

| | | | | | | |
|---|---|---|---|---|---|---|
| CTCTGCTCCC | CAAAGGATAG | TTCTGTGTCC | GTAAATCCCA | TTCTGTCACC | CCACCTACTC | 240 |
| TCTGCCCCCC | CCTTTTTTGT | TTTGAGACGG | AGTCTTGCTC | TGTCGCCCAG | GCTGGAGTGC | 300 |
| AATGGCGCGA | TCTCGGCTCA | CTGCAACCTC | CGCCTCCCGG | GTTCAAGCGA | TTCTCCTGCC | 360 |
| TCAGCCTCCT | GAGTAGCTGG | GGTTACAGCG | CCCGCCACCA | CGCTCGGCTA | ATTTTTGTAG | 420 |
| TTTTTAGTAG | AGACGAGGTT | TCACCATCTT | GGCCAGGCTG | GTCTTGAACC | CCTGACCTTG | 480 |
| TGATCCACTC | GCCTCGGCCT | TCCAAAGTGT | TGGGATTACG | GGCGTGACGA | CCGTGCCACG | 540 |
| CCCGATCTGC | CTCTTAAGTA | CATAACGGCC | CACACAGAAC | GTGTCCAACT | CCCCGCCCA | 600 |
| CGTTCCAACG | TCCTCTCCCA | CATACCTCGG | TGCCCCTTCC | ACATACCTCA | GGACCCCACC | 660 |
| CGCTTAGCTC | CATTTCCTCC | AGACGCCACC | ACCACGCGTC | CCGGAGTGCC | CCCTCCTAAA | 720 |
| GCTCCCAGCC | GTCCACCATG | CTGTGCGTTC | CTCCCTCCCT | GGCCACGGCA | GTGACCCTTC | 780 |
| TCTCCCGGGC | CCTGCTTCCC | TCTCGCGGGC | TCTCGCTGCC | TCACTTAAGC | AGCGCTGCCC | 840 |
| TTACTCCTCT | CCGCCCGGTC | CGAGCGGCCC | CTCAGCTTGC | GCGGCCCAGC | CCCGCAAGGC | 900 |
| TCCCGGTGAC | CACTAGAGGG | CGGGAGGAGC | TCCTGGCCAG | TGGTGGAGAG | TGGCAAGGAA | 960 |
| GGACCCTAGG | GTTCATCGGA | GCCCAGGTTT | ACTCCCTTAA | GTGGAAATTT | CTTCCCCCAC | 1020 |
| TCCCTCCTTG | GCTTTCTCCA | AGGAGGGAAC | CCAGGCTGCT | GGAAAGTCCG | GCTGGGGCGG | 1080 |
| GGACTGTGGG | TTTCAGGGTA | GAACTGCGTG | TGGAACGGGA | CAGGGAGCGG | TTAGAAGGGT | 1140 |
| GGGGCTATTC | CGGGAAGTGG | TGGGGGGAGG | GAGCCCAAAA | CTAGCACCTA | GTCCACTCAT | 1200 |
| TATCCAGCCC | TCTTATTTCT | CGGCCCCGCT | CTGCTTCAGT | GGACCCGGGG | AGGGCGGGA | 1260 |
| AGTGGAGTGG | GAGACCTAGG | GGTGGGCTTC | CCGACCTTGC | TGTACAGGAC | CTCGACCTAG | 1320 |
| CTGGCTTTCT | TCCCCATCCC | CACGTTAGTT | GTTGCCCTGA | GGCTAAAACT | AGAGCCCAGG | 1380 |
| GGCCCCAAGT | TCCAGACTGC | CCCTCCCCCC | TCCCCGGAG | CCAGGGAGTG | GTTGGTGAAA | 1440 |
| GGGGGAGGCC | AGCTGGAGAA | CAAACGGGTA | GTCAGGGGT | TGAGCGATTA | GAGCCCTTGT | 1500 |
| ACCCTACCCA | GGAATGGTTG | GGGAGGAGGA | GGAAGAGGTA | GGAGGTAGGG | GAGGGGCGG | 1560 |
| GGTTTTGTCA | CCTGTCACCT | GCTCCGGCTG | TGCCTAGGGC | GGGCGGGCGG | GGAGTGGGGG | 1620 |
| GACCGGTATA | AAGCGGTAGG | CGCCTGTGCC | CGCTCCACCT | CTCAAGCAGC | CAGCGCCTGC | 1680 |
| CTGAATCTGT | TCTGCCCCCT | CCCCACCCAT | TTCACCACCA | CCATG | | 1725 |

( 2 ) INFORMATION FOR SEQ ID NO: 6:

( i ) SEQUENCE CHARACTERISTICS:
        ( A ) LENGTH: 25
        ( B ) TYPE: nucleic acid
        ( C ) STRANDEDNESS: double
        ( D ) TOPOLOGY: linear ( x i ) SEQUENCE DESCRIPTION: SEQ ID NO: 6:

CCGGGAAGTG GTGGGGGGAG GGAGC        25

( 2 ) INFORMATION FOR SEQ ID NO: 7:

( i ) SEQUENCE CHARACTERISTICS:
        ( A ) LENGTH: 25
        ( B ) TYPE: nucleic acid
        ( C ) STRANDEDNESS: double
        ( D ) TOPOLOGY: linear ( x i ) SEQUENCE DESCRIPTION: SEQ ID NO: 7:

CCGGGAAGTG GCAGGGGGAG GGAGC        25

( 2 ) INFORMATION FOR SEQ ID NO: 8:

( i ) SEQUENCE CHARACTERISTICS:
  ( A ) LENGTH: 209
  ( B ) TYPE: nucleic acid
  ( C ) STRANDEDNESS: double
  ( D ) TOPOLOGY: linear ( x i ) SEQUENCE DESCRIPTION: SEQ ID NO: 8:

```
CAAGGAGGGA  ACCCAGGCTG  CTGGAAAGTC  CGGCTGGGGC  GGGGACTGTG  GGTTTCAGGG      60
TAGAACTGCG  TGTGGAACGG  GACAGGGAGC  GGTTAGAAGG  GTGGGGCTAT  TCCGGGAAGT     120
GGTGGGGGGA  GGGAGCCCAA  AACTAGCACC  TAGTCCACTC  ATTATCCAGC  CCTCTTATTT    180
CTCGGCCCCG  CTCTGCTTCA  GTGGACCCG                                         209
```

Other embodiments are within the following claims.

What is claimed is:

1. A method for treating an animal, which method comprises:
   identifying an animal suspected of having a carcinoma, and
   administering to said animal a therapeutic composition comprising a pharmaceutically acceptable carrier and a therapeutically-effective amount of a nucleic acid, wherein the nucleic acid comprises DF3 enhancer operably linked to a sequence encoding a heterologous polypeptide, wherein the polypeptide directly or indirectly produces a cytotoxic effect on carcinoma cells.

2. The method of claim 1, wherein the animal is a human.

3. The method of claim 1, wherein the therapeutic composition further comprises a gene delivery system suitable for producing transfection of an epithelial cell of said animal.

4. The method of claim 1, wherein the carcinoma is selected from the group consisting of adenocarcinoma, adrenal carcinoma, basal cell carcinoma, brain carcinoma, breast carcinoma, colon carcinoma, pancreatic carcinoma, gastric carcinoma, hepatic carcinoma, biliary system carcinoma, skin cell carcinoma, reproductive tract carcinoma, urinary organ carcinoma, small cell carcinoma, squamous-cell carcinoma, undifferentiated carcinoma, and pulmonary carcinoma.

5. The method of claim 1, wherein the DF3 enhancer comprises the nucleotide sequence of SEQ ID NO:1.

6. The method of claim 1, wherein the DF3 enhancer comprises the nucleotide sequence of SEQ ID NO:2.

7. The method of claim 1, wherein the DF3 enhancer comprises the nucleotide sequence of SEQ ID NO:3.

8. The method of claim 1, wherein the DF3 enhancer comprises the nucleotide sequence of SEQ ID NO:4.

9. The method of claim 1, wherein the heterologous polypeptide is a cytotoxic polypeptide.

10. The method of claim 9, wherein the heterologous polypeptide comprises an enzymatically active subunit of Pseudomonas exotoxin A, diphtheria toxin, Shiga toxin, Shiga-like toxin, E. coli LT, C3 toxin, pertussis toxin, tetanus toxin, cholera toxin, or botulism toxin; gelonin; ricin; tumor necrosis factor; cAMP receptor polypeptide kinase; platelet factor 4; monocyte chemoattractants; herpes virus thymidine kinase; cytosine deaminase; WTp53; retinoblastoma protein; E-cadherin; fibronectin receptor; interleukin-2; or interleukin-4.

11. The method of claim 9, wherein the nucleic acid further comprises a radiation-inducible element.

12. A method for treating an animal, which method comprises:
   identifying an animal suspected of having a carcinoma, and
   administering to said animal a therapeutic composition comprising a pharmaceutically acceptable carrier and a therapeutically-effective amount of a nucleic acid, wherein the nucleic acid comprises both DF3 enhancer and a sequence which is transcribed into an antisense RNA that inhibits expression of a target polypeptide in a cell of the animal, wherein the antisense RNA inhibits proliferation of or induces lethality in carcinoma cells.

13. The method of claim 12, wherein the target polypeptide is selected from the group consisting of N-myc, c-myb, type 1 regulatory subunit of the cAMP receptor protein kinase, and K-ras proto-oncogene.

14. The method of claim 12, wherein the animal is a human.

15. The method of claim 12, wherein the carcinoma is selected from the group consisting of adenocarcinoma, adrenal carcinoma, basal cell carcinoma, brain carcinoma, breast carcinoma, colon carcinoma, pancreatic carcinoma, gastric carcinoma, hepatic carcinoma, biliary system carcinoma, skin cell carcinoma, reproductive tract carcinoma, urinary organ carcinoma, small cell carcinoma, squamous-cell carcinoma, undifferentiated carcinoma, and pulmonary carcinoma.

16. The method of claim 12, wherein the DF3 enhancer comprises the nucleotide sequence of SEQ ID NO:1.

17. The method of claim 12, wherein the DF3 enhancer comprises the nucleotide sequence of SEQ ID NO:2.

18. The method of claim 12, wherein the DF3 enhancer comprises the nucleotide sequence of SEQ ID NO:3.

19. The method of claim 12, wherein the DF3 enhancer comprises the nucleotide sequence of SEQ ID NO:4.

20. The method of claim 12, wherein the antisense RNA inhibits proliferation of carcinoma cells.

* * * * *